(12) United States Patent
Zigha

(10) Patent No.: US 9,434,963 B2
(45) Date of Patent: Sep. 6, 2016

(54) PROCESS FOR BUTANOL PRODUCTION

(75) Inventor: Assia Zigha, Clermont Ferrand (FR)

(73) Assignee: METABOLIC EXPLORER, Saint Beauzire (FR)

( * ) Notice: Subject to any disclaimer, the term of this patent is extended or adjusted under 35 U.S.C. 154(b) by 35 days.

(21) Appl. No.: 14/382,349

(22) PCT Filed: Mar. 2, 2012

(86) PCT No.: PCT/IB2012/000758
§ 371 (c)(1),
(2), (4) Date: Sep. 2, 2014

(87) PCT Pub. No.: WO2013/128230
PCT Pub. Date: Sep. 6, 2013

(65) Prior Publication Data
US 2015/0004664 A1    Jan. 1, 2015

(51) Int. Cl.
| | | |
|---|---|---|
| *C12P 7/16* | (2006.01) |
| *C07K 14/33* | (2006.01) |
| *C12N 9/04* | (2006.01) |
| *C12N 9/02* | (2006.01) |
| *C12N 9/10* | (2006.01) |
| *C12N 9/12* | (2006.01) |
| *C12N 9/88* | (2006.01) |
| *C12N 15/52* | (2006.01) |

(52) U.S. Cl.
CPC .............. *C12P 7/16* (2013.01); *C07K 14/33* (2013.01); *C12N 9/0006* (2013.01); *C12N 9/0067* (2013.01); *C12N 9/1029* (2013.01); *C12N 9/1217* (2013.01); *C12N 9/13* (2013.01); *C12N 9/88* (2013.01); *C12N 15/52* (2013.01); *Y02E 50/10* (2013.01); *Y02P 20/52* (2015.11)

(58) Field of Classification Search
None
See application file for complete search history.

(56) References Cited

U.S. PATENT DOCUMENTS

2010/0086982 A1*  4/2010  Soucaille .................. C12P 7/16
                                                            435/160

FOREIGN PATENT DOCUMENTS

| EP | 2267126 A1 | 12/2010 |
|---|---|---|
| WO | 2004/033695 A2 | 4/2004 |
| WO | 2004/076659 A2 | 9/2004 |
| WO | 2008/040387 A1 | 4/2008 |
| WO | 2008/052596 A1 | 5/2008 |
| WO | WO/2008/052596 * | 5/2008 |

OTHER PUBLICATIONS

Gyan S, Shiohira Y, Sato I, Takeuchi M, Sato T (2006), J Bacteriol. 188:7062-7071.
Kosugi Y, Suzuki H (1992), Biotechnol. Bioeng. 40:369-374.
Lütke-Eversloh, Tina, et al, 2011, Current Opinion in Biotechnology, vol. 2, No. 5, pp. 634-647.
(Continued)

*Primary Examiner* — Alexander Kim
(74) *Attorney, Agent, or Firm* — Birch, Stewart, Kolasch & Birch, LLP

(57) ABSTRACT

This invention comprises a process for the bioconversion of a fermentable carbon source to n-butanol by a microorganism, wherein the microorganism is deficient in at least one gene or protein involved in the four-carbon compounds pathway regulation to improve the four-carbon compounds pathway, particularly by inactivation of the transcriptional repressor rex.

12 Claims, 1 Drawing Sheet

(56) References Cited

OTHER PUBLICATIONS

Montero S, Blanco A, Virto MD, Landeta LC, Agud I, Solozabal R, Lascaray JM, De Renobales M, Llama MJ, Serra JL (1993), Enzyme Microb. Technol. 15:239-247.
Pagels, Martin et al, 2010, Molecular Microbiology, vol. 76, No. 5, pp. 1142-1161.
Salah RB, Ghamghui H, Miled N, Mejdoud H, Gargouri Y (2007), J. Biosc. Bioeng. 103:368-372.
Soni BK, Goma G, Soucaille P (1987), Appl microbiol and biotechnol. 27:1-5.
Sun J, Jiang Y, Zhou L, Gao J (2010), N. Biotechnol. 27:53-58.
Tan T, Lu J, Nie K, Deng L, Wang F (2010), Biotechnol. Adv. 28:628-634.
Tummala SB, Welker NE, Papoutsakis ET (1999), Appl Environ Microbiol. 65:3793-3799.
Wang SJ, Wong DSH, Lee E-K (2003), Ind. Eng. Chem. Res. 42: 5182-5194.
Wietzke, Mandy et al, 2012, Applied Microbiology and Biotechnology, Springer, Berlin, vol. 96, No. 3, pp. 749-761.

* cited by examiner

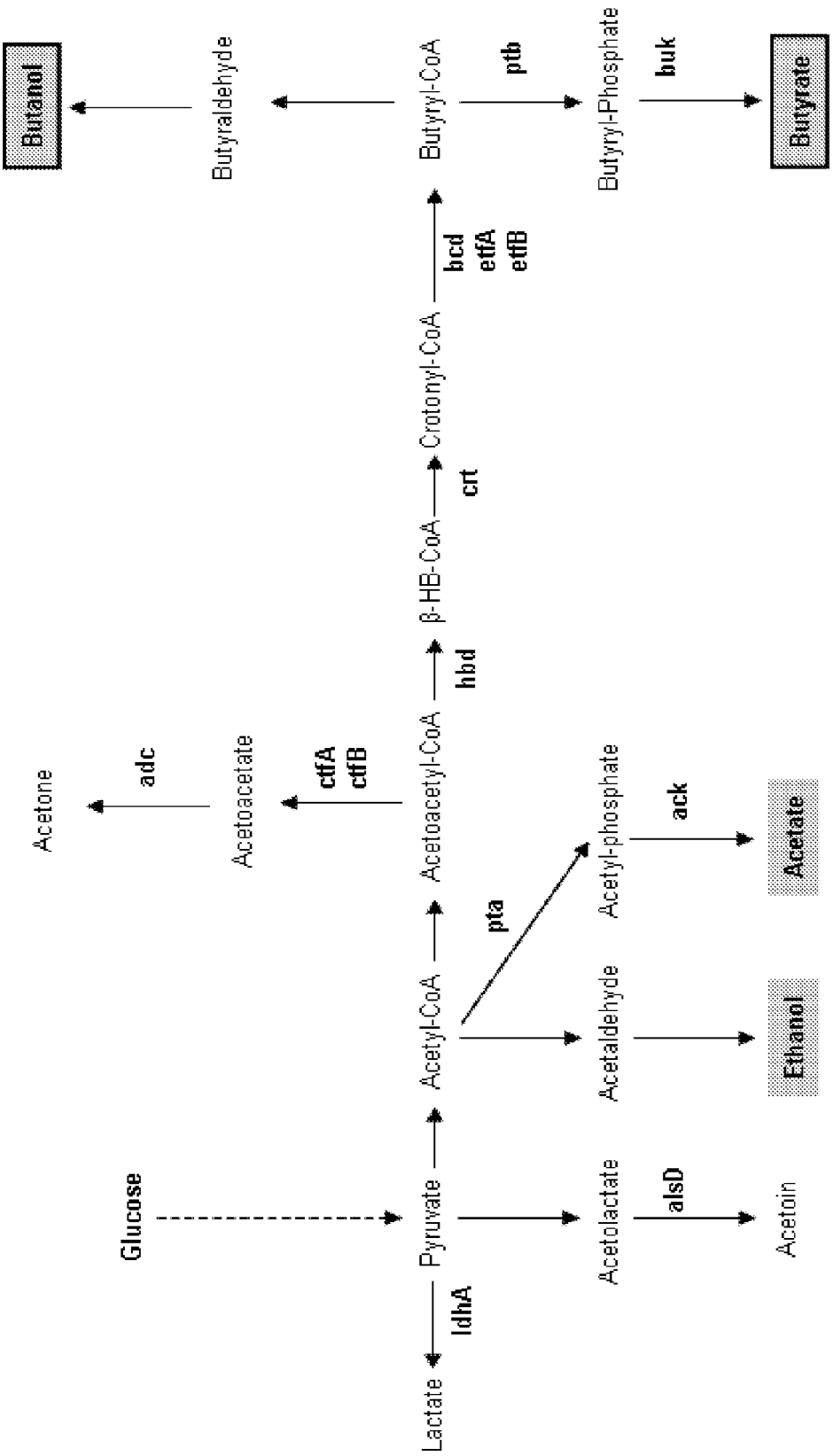

US 9,434,963 B2

SEQUENCE LISTING

<160> NUMBER OF SEQ ID NOS: 12

<210> SEQ ID NO 1
<211> LENGTH: 128
<212> TYPE: DNA
<213> ORGANISM: Artificial Sequence
<220> FEATURE:
<223> OTHER INFORMATION: Oligonucleotide

<400> SEQUENCE: 1
tacaggcctt gagcgattgt gtaggctgga gctgcttcga agttcctata ctttctagag    60
aataggaact tcggaatagg aacttcggtt ggaatggcgt gtgtgttagc caaagctcct   120

```
gcaggtcg                                                                   128

<210> SEQ ID NO 2
<211> LENGTH: 129
<212> TYPE: DNA
<213> ORGANISM: Artificial Sequence
<220> FEATURE:
<223> OTHER INFORMATION: Oligonucleotide

<400> SEQUENCE: 2
aacaggcctg ggatgtaacg cactgagaag cccatggtcc atatgaatat cctccttagt          60
tcctattccg aagttcctat tctctagaaa gtataggaac ttctcacaca ggaaacagct         120
atgaccatg                                                                 129

<210> SEQ ID NO 3
<211> LENGTH: 40
<212> TYPE: DNA
<213> ORGANISM: Artificial Sequence
<220> FEATURE:
<223> OTHER INFORMATION: Oligonucleotide

<400> SEQUENCE: 3
aaaacagctg ggaggaatga ataatgagt aaagttacac                                 40

<210> SEQ ID NO 4
<211> LENGTH: 40
<212> TYPE: DNA
<213> ORGANISM: Artificial Sequence
<220> FEATURE:
<223> OTHER INFORMATION: Oligonucleotide

<400> SEQUENCE: 4
aaaacagctg ttattttgta ccgaataatc tatctccagc                                40

<210> SEQ ID NO 5
<211> LENGTH: 51
<212> TYPE: DNA
<213> ORGANISM: Artificial Sequence
<220> FEATURE:
<223> OTHER INFORMATION: Oligonucleotide

<400> SEQUENCE: 5
aaggaaaaaa gcggccgcaa gcttacaaag tgctacacgg gttttttgcc c                   51

<210> SEQ ID NO 6
<211> LENGTH: 62
<212> TYPE: DNA
<213> ORGANISM: Artificial Sequence
<220> FEATURE:
<223> OTHER INFORMATION: Oligonucleotide

<400> SEQUENCE: 6
cattaccgta ctaatctcgg cttttttcgcg atttgaccac ctcttactta atatcacttt         60
tg                                                                         62

<210> SEQ ID NO 7
<211> LENGTH: 62
<212> TYPE: DNA
<213> ORGANISM: Artificial Sequence
<220> FEATURE:
<223> OTHER INFORMATION: Oligonucleotide

<400> SEQUENCE: 7
caaaagtgat attaagtaag aggtggtcaa atcgcgaaaa agccgagatt agtacggtaa         60
```

```
tg                                                              62

<210> SEQ ID NO 8
<211> LENGTH: 45
<212> TYPE: DNA
<213> ORGANISM: Artificial Sequence
<220> FEATURE:
<223> OTHER INFORMATION: Oligonucleotide

<400> SEQUENCE: 8
aaggaaaaaa gcggccgcaa atctttctgt ttcatcaatt tctgc               45

<210> SEQ ID NO 9
<211> LENGTH: 25
<212> TYPE: DNA
<213> ORGANISM: Artificial Sequence
<220> FEATURE:
<223> OTHER INFORMATION: Oligonucleotide

<400> SEQUENCE: 9
gcatctagga aatatctatc atgag                                     25

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide

<400> SEQUENCE: 10
gaaagaataa ctcctgtagt accgc                                     25

<210> SEQ ID NO 11
<211> LENGTH: 26
<212> TYPE: DNA
<213> ORGANISM: Artificial Sequence
<220> FEATURE:
<223> OTHER INFORMATION: Oligonucleotide

<400> SEQUENCE: 11
cacttttatt tatcaagctg taggcc                                    26

<210> SEQ ID NO 12
<211> LENGTH: 25
<212> TYPE: DNA
<213> ORGANISM: Artificial Sequence
<220> FEATURE:
<223> OTHER INFORMATION: Oligonucleotide

<400> SEQUENCE: 12 tataccttt gaacctagga aaggc                                      25
```

PROCESS FOR BUTANOL PRODUCTION

RELATED APPLICATION DATA

This application is a National Stage Application under 35 U.S.C. 371 of co-pending PCT application PCT/IB2012/000758 designating the United States and filed Mar. 2, 2012 which is hereby incorporated by reference in its entirety.

FIELD OF INVENTION

This invention comprises a process for the bioconversion of a fermentable carbon source to n-butanol by a microorganism, wherein the microorganism is deficient in at least one gene or protein involved in the four-carbon compounds pathway regulation to improve the four-carbon compounds pathway, particularly by inactivation of the transcriptional repressor rex.

BACKGROUND OF THE INVENTION n-butanol is a colorless, neutral liquid of medium volatility with restricted miscibility (about 7-8%) in water, but freely miscible with all common solvent such as glycols, ketones, alcohol, aldehydes, ethers, and aromatic and aliphatic hydrocarbons. n-butanol is used i) to make other chemicals, ii) as a solvent and iii) as an ingredient in formulated products such as cosmetics. The major uses of n-butanol as a feed-stock are in the synthesis of acrylate/methacrylate esters, glycol ethers, n-butyl acetate, amino resins and n-butylamines. Particularly n-butyl acetate is commonly used as solvent in lacquer industry and as flavour in food, beverage, cosmetic and pharmaceutical industries. Currently, more than 3.5 millions tons of n-butanol are consumed annually in the world and it has the potential to capture a significant share of the biofuels market. Thus, an interest is growing for the low cost production of n-butanol in large quantities.

n-butanol can be produced as an acetone/n-butanol/ethanol (ABE) mixture by the fermentation of carbohydrate by solventogenic *Clostridia*. Another n-butanol production process has been described in the patent application WO2008/052596. It discloses a method for the conversion of glucose to n-butanol by a recombinant *Clostridium acetobutylicum* strains modified to eliminate the butyrate pathway, the acetone pathway and the lactate pathway.

The inventors observed that in the strain inactivated for butyrate, lactate and acetone synthesis pathways, the production of two-carbon compounds (ethanol and/or acetate) is increased and thus n-butanol yields are not significantly enhanced.

The production of these two-carbon compounds suggests a regulation of expression of genes involved in the four-carbon compounds pathway. The genes involved in the four-carbon compounds pathway are located downstream of thl, a gene coding for thiolase, and are organized in an operon comprising the gene crt coding for crotonase, the gene bcd coding for butyryl-CoA dehydrogenase, the genes etfAB coding for an electron transfer protein and the gene hbd coding for beta-hydroxybutyryl-CoA dehydrogenase. A transcriptional repressor is encoded downstream of the crt-bcd-etfAB-hbd operon. This repressor is encoded by a gene (CAC2713) called rex for "redox-sensing transcriptional repressor", and is homologous to the gene rex in *Bacillus subtilis* (Gyan et al., 2006). In this study, it has been shown that the yjlC-ndh operon (coding for a NADH dehydrogenase) is negatively regulated by Rex, depending on the NADH/NAD$^+$ ratio. In the presence of high concentrations of NAD, the repressor Rex binds to the Rex box located not far from the promoter, represses the yjlC-ndh operon and also more largely the NADH consumption pathways. NAD$^+$ boosts the binding activity of Rex whilst NADH seems to have a negligible effect or a partial negative effect on DNA-binding activity.

The problem to be solved by the present invention is to improve the n-butanol production by a modified microorganism. The inventors have found that the deletion of the rex gene leads to an improved production of n-butanol by reducing the production of two-carbon compounds.

SUMMARY OF THE INVENTION

The present invention is related to a process for producing n-butanol by culturing a modified microorganism of a *Clostridium* species in an appropriate culture medium comprising a source of carbon wherein the microorganism is deficient in at least one gene or protein involved in the four-carbon compounds pathway regulation.

Deficiency in at least one gene or protein involved in the four-carbon compounds pathway regulation will provide orientation of the carbon flux in the microorganism to the four-carbon compounds pathway.

In a preferred aspect of this invention, deficiency in at least one gene or protein involved in the four-carbon compounds pathway regulation comprises inactivating or deleting the gene coding for the redox-sensing transcriptional repressor (rex).

In another aspect of the invention, the modified *Clostridium* species is further unable to metabolize butyryl-CoA to butyrate, and/or unable to produce acetone, and/or unable to produce lactate, and/or unable to produce acetate.

The modified *Clostridium* species unable to metabolize butyryl-CoA to butyrate is particularly obtained by deleting the gene coding for the butyrate kinase (buk) and/or phosphate-butyryl transferase (ptb).

The recombinant *Clostridium* species unable to produce acetone is particularly obtained by deleting the gene coding for the CoA-transferase (ctfAB) and/or aceto-acetate decarboxylase (adc).

The recombinant *Clostridium* species unable to produce lactate is particularly obtained by deleting the gene coding for the lactate-dehydrogenase (ldhA).

The recombinant *Clostridium* species unable to produce acetate is particularly constructed by deleting the genes coding for the phosphotransacetylase and/or acetate kinase (pta and ack).

In another aspect of this invention, the flux of hydrogen production in the modified *Clostridium* species is decreased compared to that of unmodified microorganism, and the flux of reducing equivalent redirected toward n-butanol production by attenuating the gene encoding the hydrogenase (hydA).

The present invention may be generally applied to include any carbon substrate that is readily converted to acetyl-CoA. Accordingly, it is an object of the present invention to provide a recombinant organism, useful for the production of n-butanol comprising the deletion of at least one gene involved in the regulation of the carbon flux to the four-carbon compounds pathway. The microorganism of the invention further comprises the deletion of: (a) at least one of the two genes involved in the conversion of butyryl-CoA to butyrate and (b) at least the deletion of one of the two genes encoding the CoA-transferase activity. Optionally, the recombinant microorganism may comprise: i) inactivating modifications in endogenous genes selected from the group consisting of: (a) a gene encoding a polypeptide having lactate dehydrogenase activity, (b) a gene encoding a polypeptide having phospho-transacetylase or acetate kinase and ii) the attenuation of a gene encoding a polypeptide having hydrogenase activity.

The invention provides a stable process for the production of n-butanol at high yield from a recombinant organism comprising (a) culturing the recombinant microorganism of the present invention with at least one carbon source selected from the group consisting of monosaccharides, oligosaccharides, polysaccharides, and single-carbon substrates whereby n-butanol is produced; optionally (b) recovering n-butanol by distillation.

In an alternative embodiment of the invention, the n-butanol obtained by fermentation of the recombinant microorganism of the invention is further converted into n-butyl acetate by condensation with acetic acid during the fermentation step or during the purification.

BRIEF DESCRIPTION OF THE DRAWINGS

FIG. 1 illustrates the two-carbon and four-carbon compounds biosynthesis pathways in *Clostridium* species. Two-carbon compounds are in the grey rectangles and four-carbon compounds are in the grey rectangles with black contours. The gene ldhA codes for the lactate dehydrogenase; alsD: acetolactate decarboxylase; pta: phosphotransacetylase; ack: acetate kinase; adc: aceto-acetate decarboxylase; ctfAB: CoA-transferase; hbd: beta-hydroxybutyryl-CoA dehydrogenase; crt: crotonase; bcd: butyryl CoA dehydrogenase; etfAB: electron transfer protein; ptb: phosphate-butyryl transferase; buk: butyrate kinase.

DETAILED DESCRIPTION OF THE INVENTION

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting, which will be limited only by the appended claims.

All publications, patents and patent applications cited herein, whether supra or infra, are hereby incorporated by reference in their entirety. However, publications mentioned herein are cited for the purpose of describing and disclosing the protocols, reagents and vectors that are reported in the publications and that might be used in connection with the invention. Nothing herein is to be construed as an admission that the invention is not entitled to antedate such disclosure by virtue of prior invention.

Furthermore, the practice of the present invention employs, unless otherwise indicated, conventional microbiological and molecular biological techniques within the skill of the art. Such techniques are well known to the skilled worker, and are explained fully in the literature. See, for example, Prescott et al. (1999) and Sambrook et al. (1989) (2001).

It must be noted that as used herein and in the appended claims, the singular forms "a", "an", and "the" include plural reference unless the context clearly dictates otherwise. Thus, for example, a reference to "a microorganism" includes a plurality of such microorganisms, and a reference to "an endogenous gene" is a reference to one or more endogenous genes, and so forth. Unless defined otherwise, all technical and scientific terms used herein have the same meanings as commonly understood by one of ordinary skill in the art to which this invention belongs. Although any material and methods similar or equivalent to those described herein can be used to practice or test the present invention, the preferred material and methods are now described. As used herein, the following terms may be used for interpretation of the claims and specification.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

As used herein the following terms may be used for interpretation of the claims and specification.

Definitions

The term "butanol" is used interchangeably with n-butanol and designates the butan-1-ol.

The term "butyl acetate" is used interchangeably with n-butyl acetate or butyl ethanoate and refers to the ester of butanol and acetic acid.

The terms "improved production of butanol" refer to either improved yield of butanol, improved titer of butanol or improved four-carbon compounds/two-carbon compounds ratio.

The term "microorganism", as used herein, refers to bacterium, yeast or fungus, which are not modified artificially.

The term "recombinant microorganism" or "genetically modified microorganism", as used herein, refers to a microorganism genetically modified or genetically engineered. It means, according to the usual meaning of these terms, that the microorganism of the invention is not found in nature and is modified either by introduction, deletion or modification of genetic elements from equivalent microorganism found in nature. It can also be transformed by forcing the development and evolution of new metabolic pathways in combining directed mutagenesis and evolution under specific selection pressure (see for instance WO2004/076659).

The terms "deficient in at least one gene or protein involved in the four-carbon compounds pathway regulation" refer to a microorganism wherein at least one gene involved in the four-carbon compounds pathway regulation is attenuated than in the unmodified microorganism and/or at least one protein involved in the four-carbon compounds pathway regulation is less active than in the unmodified microorganism.

Attenuation of genes may be achieved by means and methods known to the man skilled in the art and includes in particular gene deletion by homologous recombination, gene inactivation by insertion of an external element into the gene, gene mutation or gene expression under a weak promoter. The man skilled in the art knows a variety of promoters that exhibit different strengths and which promoter is to be used for a weak genetic expression. The term "deleted gene" means that at least 50% of genetic material has been removed or replaced by an antibiotic cassette.

The terms "inactivated" or "inactivated protein" mean to make a protein unable to function. This can be done by deleting all or part of the gene coding for the protein, or by introducing one or more mutations into the gene coding for the protein making it less active compared to unmodified protein. In case of regulatory protein, the abolishment of action of the protein may be done by deleting the binding sequence of its target genes.

In the present application, all genes are referenced with their common names and with references that give access to their nucleotidic sequences on the website http://www.ncbi.nlm.nih.gov/gene.

The activity of an enzyme is used interchangeably with the term 'function' and designates, in the context of the invention, the reaction that is catalyzed by the enzyme.

The terms "encoding" or "coding" refer to the process by which a polynucleotide, through the mechanisms of transcription and translation, produces an amino-acid sequence. The gene(s) encoding the enzyme(s) can be exogenous or endogenous.

The fermentation is generally conducted in fermenters with an appropriate culture medium adapted to the microorganism being used, containing at least one simple carbon source, and if necessary co-substrates.

An "appropriate culture medium" designates a medium (e.g., a sterile, liquid medium) comprising nutriments essential or beneficial to the maintenance and/or growth of the cell such as carbon sources or carbon substrates, nitrogen sources, for example, peptone, yeast extracts, meat extracts, malt extracts, urea, ammonium sulfate, ammonium chloride, ammonium nitrate and ammonium phosphate; phosphorus sources, for example, monopotassium phosphate or dipotassium phosphate; trace elements (e.g., metal salts), for example magnesium salts, cobalt salts and/or manganese salts; as well as growth factors such as amino acids and vitamins.

Those skilled in the art are able to define the culture conditions for the microorganisms according to the invention. In particular *Clostridia* are fermented at a temperature between 20° C. and 55° C., preferentially between 25° C. and 40° C., and more specifically about 35° C. for *C. acetobutylicum*.

The term "carbon source" or "carbon substrate" or "source of carbon" according to the present invention denotes any source of carbon that can be used by those skilled in the art to support the normal growth of a microorganism, including hexoses (such as glucose, galactose or lactose), pentoses, monosaccharides, oligosaccharides, disaccharides (such as sucrose, cellobiose or maltose), molasses, starch or its derivatives, hemicelluloses, cellulose and combinations thereof.

The terms "repressor" or "transcriptional attenuator" designate a DNA-binding protein that regulates the expression of one or more genes. Repressor proteins bind to a DNA segment named "operator". By binding to the operator, the repressor blocks the attachment of RNA polymerase to the promoter, thus preventing transcription of the genes. Alternatively the repressor stops bound RNA polymerase while transcribing DNA into RNA.

The term "repression" nominates the action of a repressor that downregulates the expression of one or more genes.

The term "recovery" means to isolate the n-butanol bioproduced from the culture medium by conventional laboratory techniques well known to the skilled worker.

The term "two-carbon pathway" refers to the biosynthesis pathways of acetate and ethanol.

The term "four-carbon pathway" refers to the biosynthesis pathways of butanol and butyrate.

The term "four-carbon compounds/two-carbon compounds ratio" refers to the titers of butanol and butyrate over the titers of acetate and ethanol.

Improved Production of n-Butanol

The present invention provides a method for the fermentative production of n-butanol by culturing a modified microorganism in an appropriate culture medium comprising a carbon source and the recovery of n-butanol from the culture medium wherein the microorganism is deficient in at least one gene involved in the four-carbon compounds pathway regulation.

Preferentially, the n-butanol production is improved. More preferentially, the four-carbon compounds/two-carbon compounds ratio is increased.

A specific embodiment of the invention provides a method wherein the microorganism is modified to improve the conversion of acetoacetyl-CoA into n-butanol due to the derepression of the crt-bcd-etfAB-hbd operon. In a preferred aspect of the invention, the microorganism is modified to be unable to produce the redox-sensing transcriptional repressor. This can be done by the inactivation or the deletion of the gene rex encoding the redox-sensing transcriptional repressor. Preferably, the gene rex is deleted.

In another aspect of the invention, action of the Rex protein is decreased. Preferentially this decrease is performed by inserting mutation in the rex gene leading to a less protein. More preferentially, action of the Rex protein is abolished by mutating or deleting the binding sequence of Rex protein named "rex box" of its target genes, in particular of the crt-bcd-etfAB-hbd operon.

Deletions of genes in *Clostridia* can be done using the method described in patent application WO2008/040387 which discloses a process for the replacement of a target DNA sequence by homologous recombination in *Clostridia*, allowing the following steps:
 i) Transforming a *Clostridium* strain with a replicative vector containing
   an origin of replication permitting its replication in *Clostridia*,
   a replacement cassette comprising a first marker gene surrounded by two sequences homologous to selected regions around the target DNA sequence, allowing the recombination of the cassette,
   a second marker gene,
 ii) Selecting strains having integrated in their genome said cassette and thus expressing the first marker gene.
 iii) Selecting strains which have eliminated said vector and thus do not express the second marker gene.

The second selection marker gene is an antibiotic resistance marker, a selection marker gene or a counter-selectable marker gene.

Another way to delete genes in *Clostridia* consists in using the method described in patent application EP 2267126 allowing the following steps:
 i) Transforming a *Clostridia* strain with a replicative vector containing
   an origin of replication functional in *Clostridia*,
   a first marker gene,
   a second marker gene,
   one or more group II intron sequences,
   a reverse transcriptase encoding gene;
 ii) Selecting strains having integrated said replicative vector and thus expressing the second marker gene;
 iii) Selecting strains having an interrupted gene following the integration of the intron sequence into said gene.

The first selection marker gene is an antibiotic resistance marker while the second selection marker gene is a counter-selectable marker gene.

Preferably, the method disclosed in patent application WO2008/040387 is used.

In another embodiment, the invention provides a method wherein the microorganism is further modified to be unable to convert butyryl-CoA to butyrate due to the deletion of at least one gene encoding phosphate-butyryl transferase (ptb) or butyrate kinase (buk). Deletion of one of these genes can be done using the method described in patent application WO2008/040387 or EP2267126. Preferably, the gene buk is deleted.

In a further embodiment of the invention, the microorganism is unable to produce acetone due to attenuation or deletion of at least one of the genes involved in acetone formation. Preferably, this gene is chosen among ctfAB encoding the CoA-transferase or adc encoding the acetoacetate decarboxylase. Deletion of one of these genes can be done using the method described in patent application WO2008/040387 or EP2267126. Preferably, the gene ctfAB is deleted.

In another embodiment of the invention, the microorganism used in the method of the invention is unable to produce lactate. In particular this can be due to a deletion of the gene ldhA coding for the lactate dehydrogenase. Deletion of ldhA can be done using the method described in the patent application WO2008/040387 or EP2267126.

In a further embodiment, the microorganism is modified in such a way to be unable to produce acetate. This result can be achieved by deletion of at least one gene involved in acetate formation. Preferably this gene is selected among the group consisting of the genes encoding phospho-transacetylase (pta) or acetate kinase (ack). Deletion of one of these genes can be done using the method described in patent application WO2008/040387 or EP2267126. Preferably, the two genes pta and ack are deleted.

An embodiment of the invention also provides a microorganism with a decreased flux of hydrogen production and then a redirection of the flux of reducing equivalent toward n-butanol production; this can be done by attenuating the gene encoding the hydrogenase (hydA), an enzyme that provides a sink for reducing equivalents in the form of hydrogen production. Attenuation of the gene hydA can be done by replacing the natural promoter by a low strength promoter or by an element destabilizing the corresponding messenger RNA or the protein. If needed, complete attenuation of the gene can also be achieved by a deletion of the corresponding DNA sequence.

Preferably, the used microorganism is selected among the group consisting of *C. acetobutylicum, C. beijerinckii, C. saccharoperbutylacetonicum* or *C. saccharobutylicum*. More preferably, the used microorganism is *C. acetobutylicum*.

An especially preferred simple carbon source is glucose. Another preferred simple carbon source is sucrose.

In another embodiment of the invention, the culture is continuous and stable.

Recovery of n-butanol during the fermentation may be accomplished by gas stripping. Preferably, the stripping gas is selected from carbon dioxide, nitrogen, air, hydrogen, or a mixture thereof. In a preferred embodiment, the stripping gas is carbon dioxide. More preferentially, the inert gas used for stripping is produced by the fermentation itself. In this case, carbon dioxide, hydrogen, or mixtures thereof produced during fermentation are for example used for the stripping step.

In a preferred embodiment of the invention, the produced n-butanol is recovered by successive distillations which allow the elimination of product with a vapour pressure greater than that of the butanol and products with a vapour pressure less than that of the butanol. These distillations are carried out according to the conventional techniques known to persons skilled in the art.

In another embodiment, the method according to the invention comprises the following steps:
  (a) contacting a microorganism with at least one carbon source selected from the group consisting of glucose, xylose, arabinose, sucrose, monosaccharides, oligosaccharides, polysaccharides, cellulose, xylan, starch or its derivatives and glycerol, whereby n-butanol is produced,
  (b) Recovering the n-butanol during the fermentation by distillation.

The fermentation is generally conducted in fermentors with inorganic culture medium of known defined composition adapted to the bacteria used, containing at least one simple carbon source, and if necessary a co-substrate necessary for the production of the metabolite.

The invention is also related to the microorganism as described previously.

Production of n-Butyl Acetate

In a specific embodiment of the invention, the recombinant microorganism produces still butanol and acetate which are converted into butyl acetate.

The two compounds may be converted into butyl acetate during the fermentation step or during the recovery step. The conversion may need a previous step of acidification of the fermentation broth in order to convert acetate into acetic acid. This acidification is achieved by adding acid in the fermentation broth or by bipolar electrodialysis.

In a first aspect, the conversion is mediated by an enzyme exhibiting lipase activity. Preferentially, this enzyme is chosen among lipase of *Candida antartica, Candida rugosa, Rhizomucor miehei, Rhizopus oryzae, Rhizopus* sp., *Rhizopus japonicus, Staphylococcus simulans, Staphylococcus warneri* and *Staphylococcus xylosus*.

In a preferred embodiment of the invention, the lipase is produced in the microorganism of the invention by expression of the corresponding gene chosen among genes coding lipase from *Candida antartica, Candida rugosa, Rhizomucor miehei, Rhizopus oryzae, Rhizopus* sp., *Rhizopus japonicus, Staphylococcus simulans, Staphylococcus warneri* and *Staphylococcus xylosus* and the conversion into butyl acetate occurs during the fermentation step.

In another preferred embodiment of the invention, the lipase is immobilised in order to improve its effectiveness. The man skilled in the art knows different supports and solvents to perform the enzyme immobilisation and how to adapt this immobilisation process to the enzyme to be immobilised as presented in the studies of Salah et al. (2007), Kosugi et al. (1992), Montero et al. (1993), Sun et al. (2010). For examples, the immobilisation of the lipase may be performed on macroporous anion exchange resin, microporous polypropylene, acrylic resin, textile membranes or diatomaceous earth in presence of solvent as for instance isooctane or glutaraldehyde.

In this aspect of the invention, the conversion is preferentially realized at an acetic acid/butanol molar ratio comprised between 3/1 to 1/5. More preferentially the acetic acid/butanol molar ratio is of 1:1.

In a second aspect, the conversion is performed by a chemical esterification directly on the fermentation broth with sulphuric acid as catalyst. Preferentially, a reactive distillation column is used as disclosed in Wang et al. (2003).

EXAMPLES

The present invention is further defined in the following examples. It should be understood that these example, while indicating preferred embodiments of the invention, are given by way of illustration only. From above disclosure and these examples, the man skilled in the art can make various changes of the invention to adapt it to various uses and conditions without modifying the essential means of the invention.

In particular, examples show modified *Clostridium acetobutylicum* strains, but these modifications can easily be performed in other microorganisms of the same family such as *C. beijerinckii*, *C. butyricum*, *C. saccharoperbutylacetonicum* or *C. saccharobutylicum*.

*Clostridium acetobutylicum* belongs to the Clostridiaceae family, which comprises members that are Gram-positive, anaerobic spore-forming bacilli, strict anaerobes for the most, and mobile in general through flagella. The genus *Clostridium* contains many species, some highly pathogenic to humans. Other species, safe for humans, are used for fermentation in the industry. Many species are involved in the decay of organic waste and are present in the soil which is their natural habitat. They can also be found in the commensal intestinal flora, especially in herbivores but also in humans. *Clostridium acetobutylicum* is one of the most important model organisms, but other important members of the Clostridiaceae family include *C. beijerinckii*, *C. butyricum*, *C. saccharoperbutylacetonicum* or *C. saccharobutylicum*.

Example 1

Plasmid Construction and Chromosomal Modification Protocol

The protocol described below was used to construct genetically different *Clostridium acetobutylicum* strains ATCC824 deleted for the rex gene or pta-ack genes as mentioned in following examples.

1.1 Construction of pUC18-FRT-Pptb-catP Vector

This plasmid contains a new CM/TH antibiotic marker "catP" functional in *Clostridia* and flanked by two FRT sites and is useful for the construction of the replacement cassettes. The "catP" gene was described in patent application WO2009/137778. The "catP" sequence, flanked by two FRT sites, two StuI sites and placed under the control of *C. acetobutylicum* phosphotransbutyrylase (ptb) promoter was amplified with Pwo DNA polymerase using pSOS94-catP as a template plasmid (WO2009/137778) and oligonucleotides FRT-CM F and FRT-CM R as primers. The PCR product was phosphorylated by T4 Polynucleotide kinase and cloned into the SmaI digested pUC18 to yield the pUC18-FRT-Pptb-catP plasmid.

| Name | SEQ ID N° | Primer sequences |
|---|---|---|
| FRT-CM F | 1 | TACAGGCCTTGAGCGATTGTGTAGGCTGGAGCTGC TTCGAAGTTCCTATACTTTCTAGAGAATAGGAACT TCGGAATAGGAACTTCGGTTGGAATGGCGTGTGTG TTAGCCAAAGCTCCTGCAGGTCG |
| FRT-CM F | 2 | AACAGGCCTGGGATGTAACGCACTGAGAAGCCCAT GGTCCATATGAATATCCTCCTTAGTTCCTATTCCG AAGTTCCTATTCTCTAGAAAGTATAGGAACTTCTC ACACAGGAAACAGCTATGACCATG |

1.2 Construction of pSOS95-MLSr-upp Vector

The upp gene with its own ribosome binding site (RBS) was cloned into the pSOS95-MLSr at the ClaI site just downstream of the MLSr gene in order to construct an artificial operon comprising MLSr and upp placed under the control of the MLSr promoter. The pSOS95-MLSr vector was obtained by SalI digestion of the pSOS95 plasmid (Tumala et al, 1999) in order to eliminate the acetone operon Pthl-ctfA-ctfB-adc.

The upp gene with its RBS was PCR amplified (Pfu) from genomic *C. acetobutylicum* DNA using oligonucleotides REP-UPP F and REP-UPP R as primers. The 664 pb PCR-product was digested by PvuII and cloned into the pSOS95-MLSr digested by ClaI and treated with T4 DNA polymerase to blunt ends. In this way, the pSOS95-MLSr-upp vector was obtained.

| Name | SEQ ID N° | Primer sequences |
|---|---|---|
| REP-UPP F | 3 | AAAACAGCTGGGAGGAATGAAATAATGAGTAAAGT TACAC |
| REP-UPP R | 4 | AAAACAGCTGTTATTTTGTACCGAATAATCTATCT CCAGC |

1.3 Construction of pSOS95-MLSr-upp-flp Vector

The flp gene of *S. cerevisiae* coding for FLP recombinase was cloned in the pSOS95-MLSr-upp vector described above under the promoter and RBS from the thiolase (thl) gene from *C. acetobutylicum* in order to reach a high level of expression in this organism. The SalI fragment containing the FLP expression cassette was obtained from the pCLF1 vector (described in patent application WO2008/040387) and cloned into the SalI digested pSOS95-MLSr-upp to yield the pSOS95-MLSr-upp-flp plasmid.

1.4 Protocol 1: Chromosomal Modification Protocol

Gene disruption in specified chromosomal loci was carried out by homologous recombination as described in patent application WO2008/040387. The thiamphenicol resistance cassette (catP) flanked by Flp recognition sites, was amplified by PCR using the pUC18-FRT-Pptb-catP plasmid as template. The resulting PCR product was used to transform the recipient *C. acetobutylicum* strain using the pSOS95-MLSr-upp plasmid harbouring the "upstream homologous region—catP—downstream homologous region" fragment with homologous regions specific to the locus to modify. Antibiotic-resistant transformants were then selected on Petri plates for clones resistant to thiamphenicol (5 µg/mL) (Tm). One colony was cultured for 24 hours in liquid synthetic medium with thiamphenicol (5 µg/mL) and 100 µL of undiluted culture was plated on 2YTG with thiamphenicol (5 µg/mL) and 5-FU (400 µM). Colonies resistant to both thiamphenicol and 5-FU were replica plated on both 2YTG with thiamphenicol (5 µg/mL) and 2YTG with clarithromycine (75 µg/mL) to select clones where 5-FU resistance is also associated with clarithromycine sensitivity. The genotype of clones resistant to thiamphenicol and sensitive to clarithromycine was checked by PCR using primers listed in examples.

The catP resistance cassette was removed by transforming the strain with plasmid pSOS95-MLSr-upp-flp expressing the flp1 gene encoding the Flp recombinase from *S. cerevisiae*. One colony of a clarithromycine resistant clone was cultured on synthetic liquid medium without clarithromycine and the culture was plated on 2YTG with 5-FU (400 µM). Colonies resistant to 5-FU were replica plated on 2YTG with clarithromycine (75 µg/mL), 2YTG with thiamphenicol (5 µg/mL) and 2YTG without antibiotic to select clones. The 5-FU resistance was associated to the loss of the pSOS95-MLSr-upp-flp vector and the thiamphenicol sensitivity to the elimination of the catP marker. The genotype of sensitive clones was checked by PCR using primers listed in examples.

Example 2

Deletion of the CAC_2713 Gene Encoding the Redox-Sensing Transcriptional Repressor Rex in *Clostridium Acetobutylicum* ATCC824

To delete the rex regulator (CAC_2713), protocol 1 is used except that couples of primers Rex 1-Rex 2 and Rex 3-Rex 4 are used to amplify the 1135 bp upstream homologous region and the 1138 bp downstream homologous region of the rex locus respectively. Both primers Rex 1 and Rex 4 introduce NotI sites while primers Rex 2 and Rex 3 have a complementary region which introduces a NruI site. DNA fragments Rex 1-Rex 2 and Rex 3-Rex 4 are joined in a PCR fusion experiment with primers Rex 1 and Rex 4 and the resulting fragment is cloned in pCR4-TOPO-Blunt (Invitrogen) to yield pTOPO:Rex. At the unique NruI site of pTOPO:Rex, the antibiotic resistance catP gene (Cm/Tm) with FRT sequences on both sides is introduced from the 1230 bp StuI fragment of pUC18-FRT-Pptb-catP. The Rex deletion cassette obtained after NotI digestion of the resulting plasmid is cloned into pSOS95-MLSr-upp at the NotI site to yield the pSOS95-MLSr-upp-Δrex-catP plasmid.

The pSOS95-MLSr-upp-Drex-catP plasmid is used to transform by electroporation the *Clostridium acetobutylicum* ATCC824 strain. The genotype of clones resistant to thiamphenicol and sensitive to clarithromycine is checked by PCR analysis (with primers Rex 0 and Rex 5 located outside of the Rex deletion cassette). The ATCC824 Δrex-catP$^R$ strain having lost pSOS95-MLSr-upp-Δrex-catP vector is isolated.

The thiamphenicol resistance of the above strain is removed according to Protocol 1. The genotype of the ATCC824 Δrex strain having lost the pSOS95-MLSr-upp-flp plasmid is checked by PCR analysis with primers Rex 0 and Rex 5.

| Name | SEQ ID N° | Primers sequences |
|---|---|---|
| Rex 1 | 5 | AAGGAAAAAAGCGGCCGCAAGCTTACAAAGTGCTACA CGGGTTTTTTGCCC |
| Rex 2 | 6 | CATTACCGTACTAATCTCGGCTTTTTCGCGATTTGAC CACCTCTTACTTAATATCACTTTTG |
| Rex 3 | 7 | CAAAAGTGATATTAAGTAAGAGGTGGTCAAATCGCGA AAAAGCCGAGATTAGTACGGTAATG |
| Rex 4 | 8 | AAGGAAAAAAGCGGCCGCAAATCTTTCTGTTTCATCA ATTTCTGC |
| Rex 0 | 9 | GCATCTAGGAAATATCTATCATGAG |
| Rex 5 | 10 | GAAAGAATAACTCCTGTAGTACCGC |

Example 3

Deletion of the CAC_2713 Gene Encoding the Redox-Sensing Transcriptional Repressor Rex in *Clostridium acetobutylicum* ATCC824 Δcac15 Δupp Δbuk ΔldhA The pSOS95-MLSr-upp-Δrex-catP plasmid as described in example 2 is used to transform by electroporation the *Clostridium acetobutylicum* Δcac15 Δupp Δbuk ΔldhA strain described in patent application WO2008/052596. The genotype of clones resistant to thiamphenicol and sensitive to clarithromycine is checked by PCR analysis (with primers Rex 0 and Rex 5 located outside of the Rex deletion cassette). The Δcac15 Δupp Δbuk ΔldhA Δrex-catP$^R$ strain having lost the pSOS95-MLSr-upp-Δrex-catP vector is isolated. The thiamphenicol resistance of the above strain is removed according to Protocol 1. The genotype of Δcac15 Δupp Δbuk ΔldhA Δrex strain having lost the pSOS95-MLSr-upp-flp plasmid is checked by PCR analysis with primers Rex 0 and Rex 5.

Example 4

Deletion of the CAC_2713 Gene Encoding the Redox-Sensing Transcriptional Repressor Rex in *Clostridium acetobutylicum* ATCC824 Δcac15 Δupp Δbuk ΔldhA ΔctfAB The pSOS95-MLSr-upp-Δrex-catP plasmid as described in example 2 is used to transform by electroporation the *Clostridium acetobutylicum* Δcac15 Δupp Δbuk ΔldhA ΔctfAB strain described in patent application WO2008/052596. The genotype of clones resistant to thiamphenicol and sensitive to clarithromycine is checked by PCR analysis (with primers Rex 0 and Rex 5 located outside of the Rex deletion cassette). The Δcac15 Δupp Δbuk ΔldhA ΔctfAB Δrex-catP$^R$ strain having lost pSOS95-MLSr-upp-Δrex-catP vector is isolated. The thiamphenicol resistance of the above strain is removed according to Protocol 1. The genotype of Δcac15 Δupp Δbuk ΔldhA ΔctfAB Δrex strain having lost the pSOS95-MLSr-upp-flp plasmid is checked by PCR analysis with primers Rex 0 and Rex 5.

Example 5

Deletion of the pta and ack Genes in *Clostridium acetobutylicum* ATCC824 Δcac15 Δupp Δbuk ΔldhA ΔctfAB Δrex To delete the pta and ack genes, we use the pta-ack deletion cassette described in patent application WO2008/052596. We use the unique StuI site of pTOPO:PA to introduce an antibiotic resistance CM/TH gene with FRT sequences on both sides from the pUC18-FRT-Pptb-catP vector. The pta-ack deletion cassette obtained after BamHI digestion of the resulting plasmid is cloned into pSOS95-MLSr-upp at the BamHI site to yield the pSOS95-MLSr-upp-DPA-catP plasmid.

The pSOS95-MLSr-upp-DPA-catP plasmid is used to transform by electroporation the *Clostridium acetobutylicum* Δcac15 Δupp Δbuk ΔldhA ΔctfAB Δrex strain. The genotype of clones resistant to thiamphenicol and sensitive to clarithromycine is checked by PCR analysis (with primers PA 0 and PA 5 located outside of the pta-ack deletion cassette). The Δcac15 Δupp Δbuk ΔldhA ΔctfAB Δrex Δpta-ack-catP$^R$ strain having lost pSOS95-MLSr-upp-Δrex-catP vector is isolated. The thiamphenicol resistance of the above strain is removed according to Protocol 1. The genotype of Δcac15 Δupp Δbuk ΔldhA ΔctfAB Δrex Δpta-ack strain having lost the pSOS95-MLSr-upp-flp plasmid is checked by PCR analysis with primers PA 0 and PA 5.

| Name | SEQ ID N° | Primers sequences |
|---|---|---|
| PA 0 | 11 | CACTTTTATTTATCAAGCTGTAGGCC |
| PA 5 | 12 | TATACCTTTTGAACCTAGGAAAGGC |

Example 6

Batch Fermentation of n-Butanol Producing Rex+ and Rex− Strains

Strains were analyzed in anaerobic flask cultures in the synthetic medium described by Soni et al., (1987) supplemented with 20 g/L of MES for strains *C. acetobutylicum* ATCC824 and *C. acetobutylicum* ATCC824 Δrex or with 2.2 g/l of acetate for strains *C. acetobutylicum* ATCC824 Δcac15 Δupp Dbuk ΔldhA ΔctfAB and *C. acetobutylicum* ATCC824 Δcac15 Δupp Δbuk ΔldhA ΔctfAB Δrex. An overnight culture at 37° C. and 150 RPM was used to inoculate a 30 ml culture to an OD620 of 0.2. After incubation of the culture for 24 h, 48 h and 72 h at 37° C. and 150 RPM, glucose, organic acids and solvents were analyzed by HPLC using a Biorad HPX 87H column for separation and a refractometer for detection.

The HPLC analyses showed that strains lacking Rex protein have a higher four-carbon compounds/two-carbon compounds ratio (butanol plus butyrate over acetate plus ethanol) than strains expressing Rex protein.

| Name of *C. acetobutylicum* strain | Butanol (g/L) | Butyrate (g/L) | Acetate (g/L) | Ethanol (g/L) | C4/C2 ratio | Butanol yield (g/g glucose) |
|---|---|---|---|---|---|---|
| ATCC824 | 6.17 | 1.45 | 1.67 | 0.45 | 3.6 | 0.2 |
| ATCC824 Δrex | 12.03 | 0.85 | 0.52 | 1.18 | 7.58 | 0.23 |
| ATCC824 Δcac15 Δupp Dbuk ΔldhA ΔctfAB | 3.22 | 0 | 5.42 | 0.38 | 0.59 | 0.17 |
| ATCC824 Δcac15 Δupp Δbuk ΔldhA ΔctfAB Δrex | 3.52 | 0 | 5.06 | 0.45 | 0.64 | 0.22 |

The deletion of the rex gene enhanced the production of butanol by increasing the ratio of four-carbon compounds/two-carbon compounds compared to unmodified microorganism, whatever the genetic context (ATCC824 Δrex or ATCC824 Δcac15 Δupp Δbuk ΔldhA ΔctfAB Δrex) and by improving titer and yield of butanol produced.

Moreover, the deletion of the rex gene led to the production of butanol (Mm: 72 g/mol) and acetate (Mm: 59 g/mol) with an almost equimolar ratio which could facilitate the butylacetate production.

REFERENCES

Gyan S, Shiohira Y, Sato I, Takeuchi M, Sato T (2006), *J Bacteriol.* 188:7062-7071

Kosugi Y, Suzuki H (1992), *Biotechnol. Bioeng.* 40:369-374

Montero S, Blanco A, Virto M D, Landeta L C, Agud I, Solozabal R, Lascaray J M, De Renobales M, Llama M J, Serra J L (1993), *Enzyme Microb. Technol.* 15:239-247

Prescott L et al. (1999), "Microbiology" 4th Edition, WCB McGraw-Hill;

Salah R B, Ghamghui H, Miled N, Mejdoud H, Gargouri Y (2007), *J. Biosc. Bioeng.* 103:368-372

Sambrook J et al. (1989) (2001), "Molecular Cloning: A Laboratory Manual" 2nd & 3rd Editions, Cold Spring Harbor Laboratory Press Soni B K, Goma G, Soucaille P (1987), *Appl microbiol and biotechnol.* 27:1-5

Sun J, Jiang Y, Zhou L, Gao J (2010), *N. Biotechnol.* 27:53-58

Tan T, Lu J, Nie K, Deng L, Wang F (2010), *Biotechnol. Adv.* 28:628-634

Tummala S B, Welker N E, Papoutsakis E T (1999), *Appl Environ Microbiol.* 65:3793-3799

Wang S J, Wong D S H, Lee E-K (2003), *Ind. Eng. Chem. Res.* 42: 5182-5194

The invention claimed is:

1. A method for the production of n-butanol comprising culturing a modified microorganism of a *Clostridium* species in an appropriate culture medium comprising a source of carbon, wherein said modified microorganism has at least the gene rex encoding a redox-sensing transcriptional repressor recombinantly inactivated or deleted.

2. The method of claim 1, wherein the recombinant inactivation or deletion results in action of the Rex protein being decreased by mutating or deleting binding sequences of the Rex protein which binds to its target genes.

3. The method of claim 1, wherein in the modified microorganism at least one of the following genes involved in butyrate formation is deleted:
   buk encoding butyrate kinase,
   ptb encoding phosphate-butyryl transferase.

4. The method of claim 1, wherein in the modified microorganism at least one of the following genes involved in acetone formation is deleted:
   ctfAB encoding CoA-transferase
   adc encoding aceto-acetate decarboxylase.

5. The method of claim 1, wherein in the modified microorganism at least one of the following genes involved in acetate formation is deleted:

pta encoding phospho-transacetylase ack encoding acetate kinase.

6. The method of claim 1, wherein in the modified microorganism the gene IdhA involved in lactate formation is deleted.

7. The method of claim 1, wherein the hydrogen flux in the modified microorganism is decreased by an attenuation of the gene hydA.

8. The method of claim 1, wherein the modified microorganism is selected among the group consisting of *C. acetobutylicum, C. beijerinckii, C. saccharoperbutylacetonicum* and *C. saccharobutylicum*.

9. The method of claim 1, further comprising converting n-butanol into n-butyl acetate with acetic acid during the culturing step or during a recovery step of n-butanol.

10. The method claim 1, wherein n-butanol is recovered from the culture medium by successive distillations.

11. A microorganism of *Clostridium* species, useful for the production of n-butanol from a carbon source, wherein said microorganism comprises recombinant inactivation or deletion of the gene rex.

12. The microorganism of claim 11, wherein said microorganism comprises at least one of the following modifications:

deletion of the genes ptb, buk, ctfAB, adc, pta, ack, ldhA
  attenuation of the gene hydA.

* * * * *